United States Patent [19]

Hossom et al.

[11] Patent Number: 4,623,461

[45] Date of Patent: Nov. 18, 1986

[54] TRANSVERSE FLOW DIAGNOSTIC DEVICE

[75] Inventors: Miles G. Hossom, Duluth, Ga.; Dinesh A. Jacob, Girton, United Kingdom

[73] Assignee: Murex Corporation, Norcross, Ga.

[21] Appl. No.: 740,100

[22] Filed: May 31, 1985

[51] Int. Cl.⁴ .......................................... B01D 29/04
[52] U.S. Cl. .................................. 210/445; 210/451; 210/453; 210/455; 210/469; 210/474; 210/477; 422/101
[58] Field of Search ................ 422/101; 435/177–182; 436/137, 138, 530, 531; 210/446, 451, 455, 469, 474, 477, 445, 453, 456, 478, 541, 483, 448, 452

[56] References Cited

U.S. PATENT DOCUMENTS

| | | | |
|---|---|---|---|
| 3,552,925 | 1/1971 | Fetter | 23/230 |
| 3,645,687 | 2/1972 | Nerenberg | 23/230 R |
| 3,825,410 | 7/1974 | Bagshawe | 23/230 R |
| 3,888,629 | 6/1975 | Bagshawe | 23/230 B |
| 4,059,405 | 7/1977 | Sodickson et al. | 23/230 R |
| 4,116,844 | 9/1978 | Hein et al. | 210/477 |
| 4,246,339 | 1/1981 | Cole et al. | 23/230 B |
| 4,270,920 | 6/1981 | Kondo et al. | 23/230 B |
| 4,366,241 | 12/1982 | Tom et al. | 435/7 |
| 4,407,943 | 8/1983 | Cole et al. | 435/7 |
| 4,477,575 | 8/1984 | Vogel et al. | 436/170 |
| 4,517,288 | 5/1985 | Giesel et al. | 435/7 |

FOREIGN PATENT DOCUMENTS 0141547 5/1985 European Pat. Off. .

Primary Examiner—Frank Sever
Attorney, Agent, or Firm—Sigalos & Levine

[57] ABSTRACT

This invention relates to a device for testing a specimen comprising a liquid input means having a receiving inlet and a discharge aperture, filter means positioned below the input means having at least one reaction zone for receiving liquid from the input means and at least one peripheral zone associated with the at least one reaction zone, absorbent means associated with only the peripheral zone of the filter means, and retainer means for holding the filter means in position below the liquid input means such that the at least one reaction zone receives liquid therefrom.

41 Claims, 10 Drawing Figures

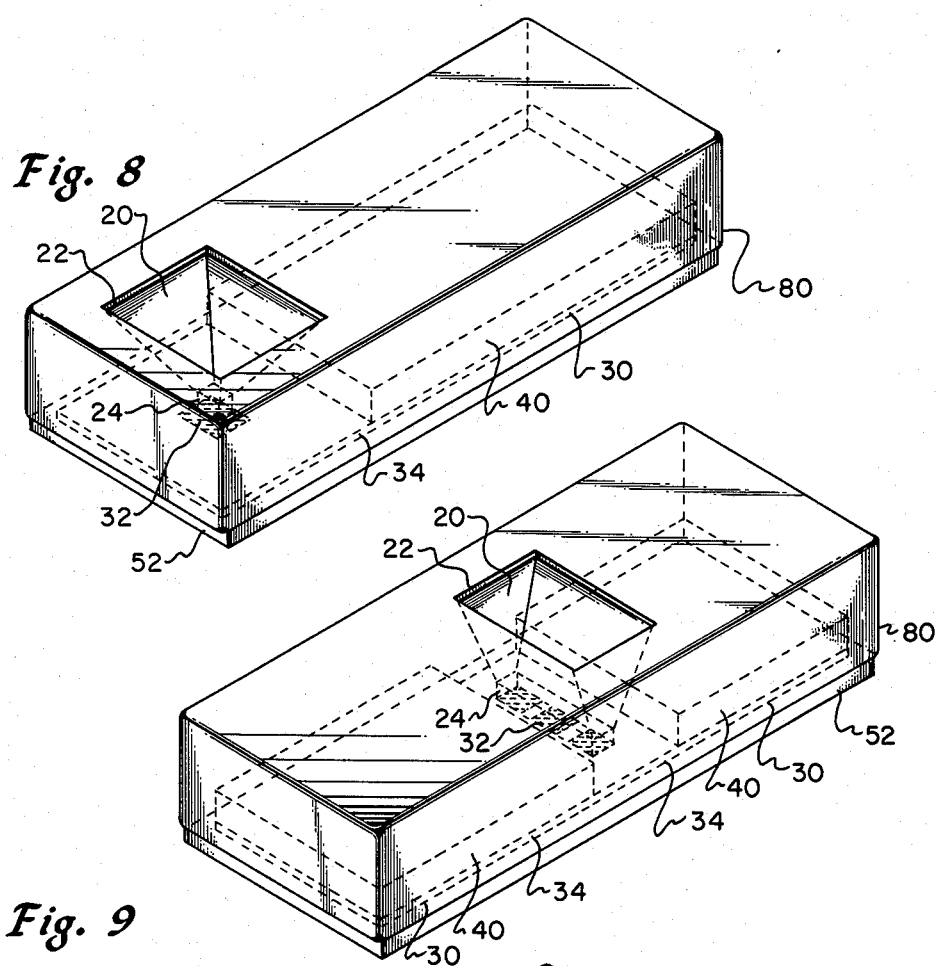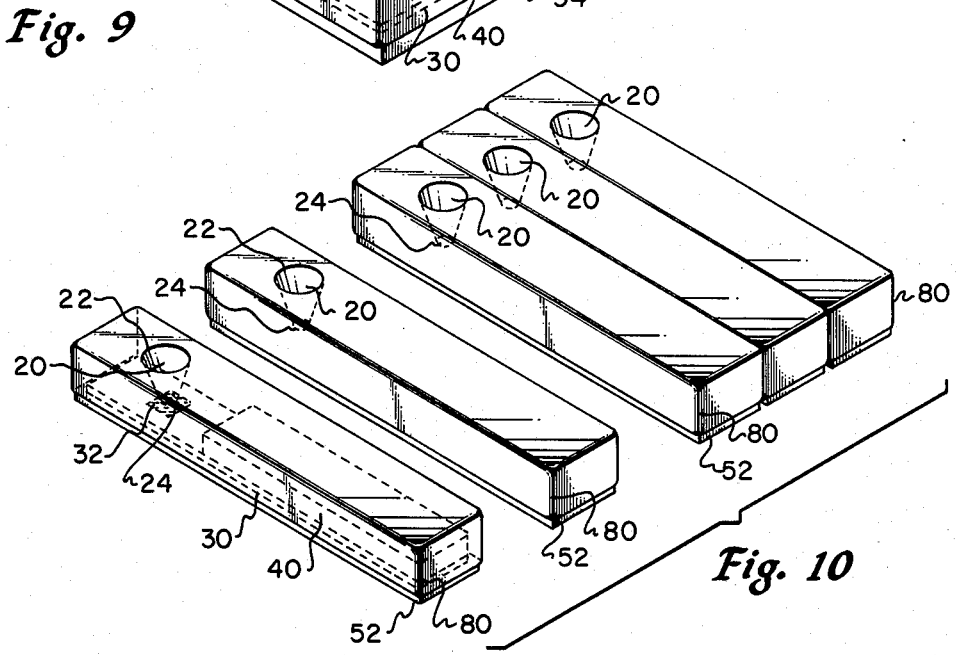

TRANSVERSE FLOW DIAGNOSTIC DEVICE

BACKGROUND OF THE INVENTION

The present invention relates to diagnostic devices for analyte assay. More particularly it relates to devices and methods utilizing filter means for testing biological fluids to detect the presence of analytes such as bacterial, viral, parasitic, or fungal antigens and immunoglobulins, hormones, serum proteins, drugs, and the like.

At the present time there are a number of devices and procedures disclosed for diagnosing for the presence of such analytes by means of reaction occurring on filters but they are either too complex, costly, inaccurate, time-consuming or a combination of such factors.

For example, U.S. Pat. No. 3,888,629 discloses a reaction cell having a matrix pad for carrying out immunoassays. The pad serves as the means for retaining the reagents and as the site in which the reaction occurs and one or more of the fluid reagents are added to the pad and pass therethrough to the absorbent material directly below. In addition to the many time-consuming steps required to process the pad to determine the results of the test; including removing it from the device, such device is essentially limited to isotopic tests. It is not practical for nonisotopic tests such as enzyme-linked immunoassays, since the device requires removal of the absorbent pad for viewing. Moreover, certain biological fluids, such as blood sera, contain particulate and/or colored matter which tend to remain on the surface of the matrix pad and thus make it difficult, if not impossible, to obtain an accurate reading in nonisotopic immunoassay procedures. Further, by passing the reagents directly through the entire surface area of the matrix pad there is often poor separation of the analyte since the absorbent pad is very thin (thereby affording only a very short distance for a separation to occur) and there is limited concentration of analyte at any location on or in the pad.

Efforts to improve such device are reflected in U.S. Pat. Nos. 4,246,339 and 4,407,943 which try to limit the area of the fiber through which one or more of the reagents must pass. Here again, however, there is flow directly through the thin filter to the absorbent material below the filter resulting again in poor separation and difficulty in obtaining accurate readings when specimens are being tested which contain particulate and/or colored matter which is retained on the surface of the filter.

SUMMARY OF THE INVENTION

The present invention obviates the problems of the prior devices and provides devices for rapid and accurate analyte assay.

Briefly, the present invention comprises a device for testing a specimen comprising a liquid input means having a receiving inlet and a discharge aperture; filter means positioned below said input means having at least one reaction zone for receiving liquid from said input means and at least one peripheral zone associated with said at least one reaction zone; absorbent means associated with only said peripheral zone of said filter means; and retainer means for holding said filter means in position below said liquid input means such that said at least one reaction zone receives liquid therefrom.

BRIEF DESCRIPTION OF THE DRAWINGS

FIG. 8 is yet another alternative embodiment having liquid dispensing means positioned at one end of the device and absorbent material at the remaining space.

FIG. 9 is an embodiment having liquid dispensing means shaped as a trough containing a plurality of discrete liquid discharge apertures contacting filter means defining a plurality of reaction zones.

FIG. 10 is an embodiment showing a combination of individual devices joined together.

DETAILED DESCRIPTION OF THE DRAWINGS

The device of the present invention is suitable for use with any of the conventional procedures used for analyte assays such as isotopic assays and nonisotopic assays such as competitive or non-competitive enzyme-linked immunoassays, enzyme multiplied immunoassays, enzyme inhibition immunoassays, heterogeneous or homogeneous fluorescent immunoasays, chemiluminescent and bioluminescent assays, those assays using labeled RNA or DNA probes, and the like.

The particular analyte assay test to be used will depend upon the particular analyte and the desire of the person carrying out the test. The only essential requirement for each particular test used is that the device of the instant invention be structured, as discussed below, so as to insure that all fluids and reactants necessary to carry out the test are caused to flow outwardly through the filter means from the point of application onto a localized portion of the top surface of the filter to peripheral portions in the filter and that no fluid passes completely through the filter at the point of application. This critical aspect of this invention results in better separation of analyte since it travels further transversely through the filter means, concentration of all the analyte and other reactants at a localized portion of the filter means resulting in more accurate results, and permits top, bottom, and straight-through reading of the filter means to determine the results of the test.

Other than this requirement of the present invention, all of the other steps, conditions, reactants, and the like of the various conventional analyte assays set forth above are those conventionally used in such procedures.

The invention can be more fully understood with reference to the drawings in which like numerals represent like elements.

Figure 1:
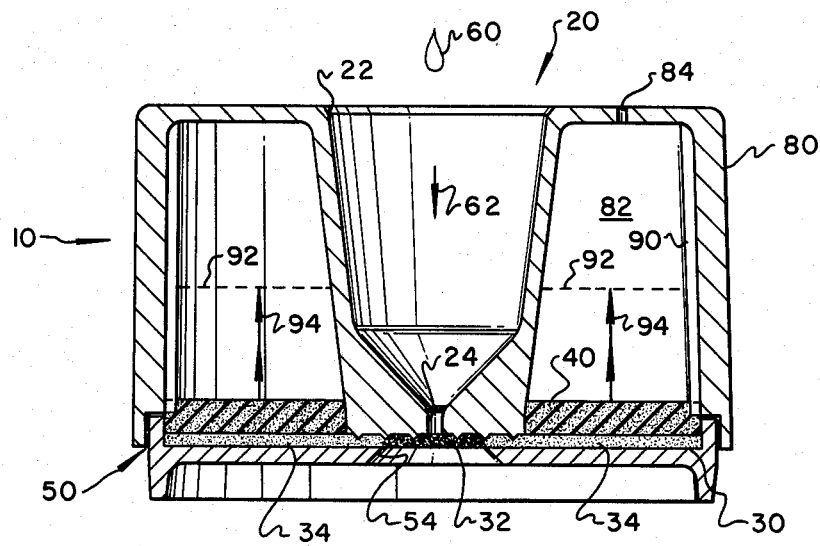
FIG. 1 is a cross-sectional view of a test device of the present invention.

The basic operation of the inventive test device can be understood with reference to FIG. 1 in which the test device 10 comprises a liquid input means 20 with a filter means 30 positioned below said input means 20 having a reaction zone 32 for receiving the liquid from said liquid input means 20 and a peripheral zone 34 associated with the reaction zone 32. Associated with only the peripheral zone 34 of filter means 30 is an absorbent means 40. Further, there is a retainer means 50 comprised of closure member 52 for holding the filter means 30 in position below the input means 20 such that the reaction zone 32 receives liquid 60 from said liquid input means 20. Thus, it can be understood that a liquid placed or poured into receiving inlet 22 of input means 20 will flow through discharge aperture 24 into reaction zone 32 of filter means 30. Liquid 60 passes through filter means 30 transversely from reaction zone 32 into peripheral zone 34. A reaction, such as filter separation or immunological binding, may take place in the reaction zone 32 as the liquid is diffused therethrough and color changes or other reaction reading signals produced in the reaction zone 32 can be viewed or read through viewing port 54 in closure means 52. The unreacted liquid is absorbed by absorbent means 40 which is in contact only with the peripheral zone 34 without directly contacting reaction zone 32. Thus, the liquid passes through reaction zone 32 before being absorbed. The absorbent means 40 is positioned within hollow cavity 82 formed within casing means 80 which is removably or permanently press-fit onto closure means 52. As liquid is absorbed by absorbent means 40, air within hollow cavity 82 is displaced by the liquid. The displaced air escapes through vent 84 so that the air pressure is equalized. All components other than the filter means 30 and the absorbent means 40, the construction of which will be described below, may be formed of any suitable inert material such as molded polystyrene or another plastic material. The material is preferably opaque and preferably white in color so that color interference with the reaction signal is reduced.

The liquid depends upon the test, assay or immunoassay being performed. In any given test more than one type of liquid may be used in a predetermined sequence. For example, a fluid used to prepare the reaction zone may be added, then a washing fluid or solvent, then a bodily fluid specimen and then another washing liquid, then a reaction indicator fluid or coloring agent and then another washing fluid. The capacity of the absorbent means must be sufficient to handle all the liquid used in the test. The large capacity of the inventive device allows the user added flexibility in the tests which can be performed. Also an inert reaction zone 32 can be used because the device has sufficient capacity for preparatory additions of liquid.

The liquid input into the liquid input means flows in liquid flow direction 62. It being understood that in the preferred embodiment the motivating force of the flow is gravity such that the liquid flows through liquid input means 20 generally from top to bottom or from receiving inlet 22 to discharge aperture 24.

The liquid flows through discharge aperture 24 onto filter means 30 positioned below the input means 20. Filter means 30 has at least one reaction zone 32 for receiving liquid from said input means. Also filter means 30 has at least one peripheral zone 34 associated with the reaction zone 32. The diameter of discharge aperture 24 is sufficient in connection with the liquid head pressure present in input means 20 so that the liquid will discharge onto upper surface 37 of filter means 30 and will not be forced straight through the filter 30 and out the bottom surface 39. Thus, the hydrostatic pressure is adjusted so that the liquid enters the filter by gravitational forces and it is diffused through the filter 30 by capillary action. It has been found that, for an input funnel 20 which is approximately 1.2 inches high and a filter 30 which is 0.03 inch thick, a discharge aperture having an approximate diameter of 0.06 inches is sufficient. Absorbent means 40 acts to ensure this outward flow so that no liquid goes completely through filter means 30 at the point of application from input means 20. Thus, the diameter and height of the discharge aperture 24, type and thickness of filter means 30, and type and thickness of absorbent means 40 are correlated to ensure that all liquid used for any particular assay will not be passed straight through the filter, but will travel transversely outwardly from the point of application in the filter plane. The particular dimensions for each assay procedure can be readily determined by routine experimentation.

A unique aspect of the present invention is the combination of the pushing force of gravity and the outward transverse pulling force of the capillary action of the filter means 30 and absorbent means 40. Other devices commercially available make use of predominantly either only a pushing force or a pulling force. Examples of such devices are those that drop compounds onto the filter via a pipette, relying on a "radial" flow of fluid through the filter, or a reservoir means whereby a column of fluid is drawn straight through the filter without any transverse flow of fluid along the plane of the filter. The present invention employs both forces so that a column of fluid is pushed onto the filter by hydrostatic pressure, and subsequently drawn by capillary action outward through the filter from the point of application to a peripheral zone and then into the absorbent means. The use of these motivating forces effects a more rapid and complete filtration and separation of components in the filter means.

In the preferred embodiment the filter means 30 is made of a porous material capable of drawing liquid within its structure by capillary action. The pores of the filter 30 should be sufficiently small to effect a filter separation of an insolubilized component within the liquid from a solubilized component. The filter may be composed of materials such as glass fiber filter paper, nitrocellulose, plastic, synthetic polymer, cellulose, cellulose acetate, polytetrafluoroethylene, polyethylene, polypropylene, polyvinylidene fluoride, or any other material formable into a filter having the qualities and characteristics as described above. In many applications it is desirable to use a material which is inert and chemically nonreactive with the analytes and washing solvents with which the test device is to be used. It has been found that a filter means, which comprises a microporous membrane having substantially uniform pores between 25 nanometers and 25 micrometers, has the characteristics described and is useful in performing immunoassay testing procedures for which this device is particularly useful. Examples of filters which may be used include filter paper known as WHATMAN GF/D and filter disc made by MICRO FILTRATION SYSTEMS of borosilicate glass known as GD-120 standard filter discs.

The apparatus of the present invention is beneficial where chemical reactions (typically the immunochemical reactions) occur external to the device and the final reactants fed into the filter means for separation of the unreacted elements therefrom. In external reactions, improved accuracy of component addition is possible.

It is generally accepted that a longer incubation period can afford more complete reaction and binding of the reactants, thereby increasing the sensitivity of the assay systems that conduct the reactions solely within the filter means frequently are limited in the length of the incubation period. The filter can dry out during long incubation periods with such systems decreasing the sensitivity of the assay. In the present invention, because the reactants can take place externally to the device, much greater control and flexibility are obtained over the incubation period, greatly improving the overall sensitivity and specificity of the assay. In such instances the device is used primarily as a separation device to separate soluble components from insoluble components within the liquid specimen poured into the input 20 of the inventive test device 10. Thus, where it is desirable to perform numerous and varied assays without having a specific device for each specific assay, the inventive test device is useful. Such a nonspecific device may be composed of inert materials and therefore may be stored for an indefinite period of time and without refrigeration. Moreover, such nonspecific devices can be produced using mass production techniques at substantial cost savings.

The device 10 may also be used for specific immunochemical assays by "prespotting" the reaction zone with an analyte specific reactant. Prespotting is a term used to indicate that in a localized region 36 of filter means 30, such as within reaction zone 32 only, an analyte specific reactant may be immobilized on the internal surfaces of the filter material. These internal surfaces define the interstices within the structure of the filter material. In prespotting, the reaction zone 32 of the device is prepared for direct use of a test specimen often without preparatory additions to the test device. For example, the manufacturer of the device could place in the filter reaction zone a binding protein to which an antibody is bound, which antibody is immunologically reactive with a specific antigen. Thus, a specimen being tested for the specific antigen would be poured into the test device inlet, flow through the discharge aperture and would be discharged onto the upper surface 37 of reaction zone 32 of filter 30. The solution would be wicked through the reaction zone 32 which has been prespotted at 36. After a sufficient incubation time, a washing solution would be added to the device and is again wicked through the reaction zone, washing unreacted components of the specimen outward into the peripheral zone, and into the absorbent means, thus stopping the immunological reaction. If the specific antigen is present in the specimen, it binds to the antigen's specific antibody which itself is already immobilized within the filter and would remain in the reaction zone after the washing step. The unbound antigen and other material within the solution are effectively washed away from the reaction zone and into the absorbent means 40. Finally, an antibody labeled with a detectable enzyme, such as an enzyme which generates a particular color of light, is poured through the test device and binds to the bound antigen. A washing solution is again added after a desired incubation period to remove all unbound enzyme labeled antibodies. Then the reaction zone is viewed through the viewing port 54 to determine if the color produced by the enzyme is present and, if so, in what amounts. The presence of the enzyme indirectly indicates that the antigen was indeed within the sample specimen. The absence of the enzyme indicates no antigen was present.

Figure 2:
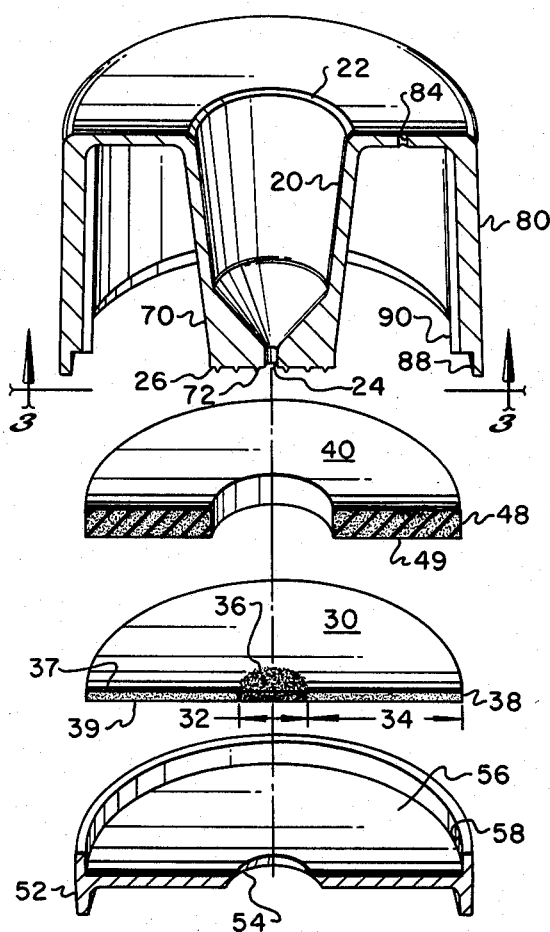
FIG. 2 is an exploded perspective cross-sectional view of the test device.
Figure 3:
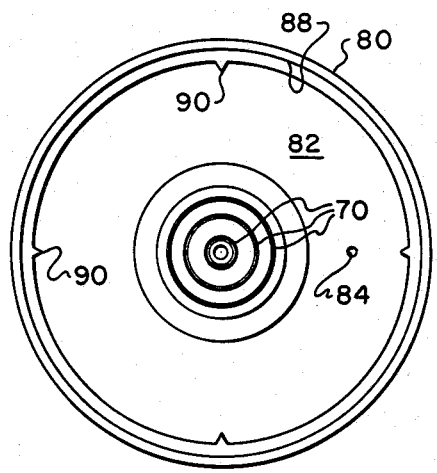
FIG. 3 is a bottom view of the dispensing means and a portion of the casing means.

As shown in FIG. 2, the preferred embodiment of the test device is formed substantially symmetrically around a vertical axis. The absorbent means 40 is a skirt 40 of absorbent material which entirely surrounds the discharge aperture 24 of the input funnel 20. The absorbent material may be any suitable material such as hydrophilic polymers, particulate absorbents, glass fiber, cotton fiber, cellulose fiber, wood pulp, or sponge material. In the preferred embodiment a compressed sponge material is used which expands upon absorbing liquid. In other embodiments of this invention absorbent means 40 may be positioned partially encompassing the periphery of reaction zone 32, such as in FIGS. 7, 8, and 9.

The filter means 30 is formed in a flat circular disc shape. The closure means 52 is of a size and shape corresponding to the filter means 30. This configuration promotes uniform flow outwardly from the point at which liquid is discharged from discharge aperture 24 and onto reaction zone 32. The uniform flow outwardly through filter 30 as provided by this inventive test device is advantageous over other test devices for several reasons. It is desirable to have all of the specimen pass through a localized zone of the filter material, and to have relatively large quantities of liquid pass through the localized zone. This is accomplished by making the receiving inlet 22 larger than the discharge aperture 24 so that large quantities of liquid are funneled for localized discharge onto the reaction zone 32. The outward flow permits a large area of absorbent material to be in contact with the filter so that large quantities of liquid can pass through the filter means while maintaining a small reaction zone. Further, to promote the passage of the liquid through the reaction zone rather than merely spreading across the surface of the filter, a substantially liquid impermeable shield 70 contacts the surface of the filter means 30 separating the discharge aperture 24 from the absorbent means 40.

It is important that fluid applied to the reaction zone area pass into the filter means and flow outwardly into the absorbent means. Flow of fluid across the top of the filter means must be impeded so as to ensure the chromatographic separation of the bound from unbound materials via capillary action. As shown in FIG. 2, the shield means 70 is provided by abutting the bottom end 26 of the liquid input means 20 against the filter means 30. The shielding action is promoted by having at least one serration 72 which contacts the upper surface of the filter means and compresses it slightly to provide an impediment to surface flow so that the liquid is directed into and must pass through at least a portion of the reaction zone 32 structure via the interstices within the reaction zone of the filter means 30. To promote complete shielding with minimum localized compression of filter means 30, multiple serrations are used in the preferred embodiment as shown in the drawings. Alternatively, the shield means 70 can be permanently affixed to the filter means, ensuring the separation of the discharge aperture from the absorbent means.

A unique aspect of the present invention is the ability to read and illuminate from either the top or bottom surface. Other systems are limited to reading the reaction from either only the top or only the bottom surface and typically require illumination from the same side as it is being read; these include filter discs, dipsticks, tabs containing filter materials, devices where the illumination opening and the reading opening are the same, etc. The capability of reading from either surface enhances the flexibility and adaptability of the present invention to different reaction systems. A beneficial aspect of the inventive test device is that the reaction zone can be viewed from the bottom. As shown in FIG. 2, closure means 52 has formed therein a viewing port which is held in alignment with the reaction zone of the filter means. In the embodiment shown the filter means 30 is a flat circular disc shape, the absorbent means 40 is in the shape of an annular ring, and the reaction zone is a circular disc shape. The viewing port 54 permits easy viewing of the bottom face 39 of the reaction zone 32 without any interference or obstruction caused by either the input means 20 itself, or by debris and particulate or colored matter which may have been present in the liquid specimen. It is especially advantageous to have a device which permits bottom reading where the liquid specimen comprises bodily fluids such as blood, urine, feces, mucus, or other specimens which may be colored or in which contaminants may be present. Such contaminants include colored red blood cells, dead cellular materials from mucosal specimens, various colored debris, and food particles from feces, crystalline or other precipitates from urine, etc. The prior art devices require that the samples be cleansed of particulate matter as by centrifuge devices prior to testing. Viewing port 54 is made sufficiently large to allow light to enter so that an accurate reaction reading can be made. The test device is versatile and the reaction can also be read by illuminating the top surface and reading from said through liquid input means 20 where such a reading is desirable, as where the sample specimen is relatively free of particulate matter or as where the particulate matter entrapped near the upper face of the reaction is of particular importance to the test. Moreover, with the present test device it is possible to illuminate from the top surface and read the bottom surface, or, illuminate the bottom surface and read from the top. This unique ability permits convenient instrument reading of samples by measuring the absorbance of light by material present in the filter. An assay particularly well suited for this is an enzyme substrate system whereby the density of substrate as related to the presence of analyte is measured by the increased absorbance of light passing through the filter. Since either surface can be read from, the advantage is in its adaptability to different instruments.

The liquid impermeable shield 70 can be designed to enhance the readability of the reaction by having the bottom surface of the shield be either light absorbency, light reflecting, or light transmitting, depending on the desired method of reading the reaction. For example, when it is desired to both illuminate and read from the bottom surface, a reflection surface at which light received through the filter will reflect off the sample and exit the bottom surface, thereby enhancing readability of the reaction. When it is desirable to eliminate reflection, reading through the filter by illuminating the opposite surface can be enhanced by designing the shield to be light transmitting; in this manner the instrument reading can be improved.

As can be seen with reference to FIG. 2, enclosure means 52 provides a flat surface 56 to support the substantially flat bottom face 39 of the peripheral zone 34 of filter means 30. Also alignment means 58, which may be a circular ridge 58 integrally formed on holding means 52 has an inside diameter corresponding to the outside diameter 38 of filter disc 30 and an outside diameter corresponding to the inside diameter of lip 88 of casing 80. Likewise, absorbent means 40 has an outside diameter 48 corresponding to the outside diameter 38 of filter means 30 and the inside diameter of alignment means 58. Thus, all the component parts of the invention are fitted together and thereby held in alignment. In particular, the reaction zone 32 is held aligned with discharge aperture 24 for receiving liquid therefrom. Alignment of the reaction zone and the discharge aperture is crucial for accurate reproducible results. The funneling means consistently delivers fluid precisely to the same position on the filter via the discharge aperture, thereby eliminating random positioning errors by manual manipulations or mechanical means. The accurate positioning of fluids onto substantially the center of the reaction zone affords greater accuracy. Where the reaction occurs external to the device, all fluids added to the device are guaranteed to be applied to the same point because of this alignment. Furthermore, where the filter is prespotted with a component, such as an antibody, accuracy is ensured by the correct addition of antigen and wash fluids precisely to the prespotted area. Other devices introduce user error by not having a fluid delivery system funneling means aligned with the reaction zone of each device. Some other systems have a large area of filter containing a small reaction zone whereby a user must approximate where the colorless prespotted component is. If not located precisely in the center, incomplete binding or washing can occur, reducing the overall accuracy and sensitivity of the assay.

The upper face 37 of the filter 30 will trap colored or particulate matter contained within the specimen and prevent such insoluble matter from reaching the bottom face 39 of the reaction zone 32. Only the soluble material will diffuse outwardly through the filter and down to the bottom face 39. The reading port 54 as described above is held in alignment with the reaction zone to afford a reaction reading signal that is free from false coloration or extraneous matter.

To provide maximum separation of bound from unbound label and thereby reduce background noise during observation of the reaction, the invention provides for outward diffusion of liquid applied to the filter toward the absorbent material 40. The filter material 30 serves not only as a means for trapping and immobilizing, but also as a means for liquid transfer from the point of application to the absorbent material 40 so as to effect a filter separation. Diffusion of the material outward from the center point of application rather than directly down through the filter provides a more effective separation, particularly during the washing step where the unbound components are to be removed from the bound components. Properly performed in the present inventive apparatus an assay procedure will leave a concentrated spot of bound label in the reaction zone 32 of the filter material, immediately surrounding the reaction zone 32 will be clear peripheral zone 34 containing negligible signal generating material, and the unbound label will be washed away from the observation area of the reaction zone.

To maximize the contrasting zones, relatively large quantities of washing solution are required. To promote effective transfer of the relatively large quantity of liquid from the peripheral zone 34 to the absorbent means 40, the annular ring 40 of absorbent material is held in intimate contact with a portion of peripheral zone 34. A large transfer area can be accomplished by forming the annular absorbent ring in the shape of a hollow cylinder of substantially uniform thickness having a flat base 49 which is held in intimate contact with the upper face 37 of the peripheral zone 34 of the filter means 30. Continuous and complete contact is promoted by forming at least one, and preferably more than one, evenly-spaced projections 90 on the internal surface of cavity 82. Frictional contact between absorbent means 40 and projections 90 acts to restrict the movement of absorbent means 40 upward into the hollow cavity 82. Thus, it is held in intimate contact with the filter surface for direct transfer of liquid therefrom.

Where the hollow cylinder absorbent material is compressed sponge material, it will be relatively rigid in its dry state and will become more flexible upon absorbing liquid and expanding. The additional flexibility permits the absorbent material to expand deforming slightly to accommodate projections 90 as it expands into hollow cavity 82. The air displaced thereby is permitted to escape through vent 84. As shown in FIG. 1 by dashed lines 92 and directional arrows 94, the compressed absorbent material may expand several times its original thickness upon absorbing the substantial amount liquid used in the testing device.

The absorbent material makes possible the use of a very large volume of wash fluid. Generally, a more effective separation is obtained when using large wash volumes. In other devices not containing absorbent material, the amount of wash solution that can be used is limited by the absorbent characteristics of the filter material, typically much less than an absorbent material such as a sponge or compressed wood pulp material.

While the invention thus far has been described with respect to a preferred embodiment, reference to FIGS. 4, 5, 6, 7, 8, 9, and 10 shows additional alternative embodiments.

Figure 4:
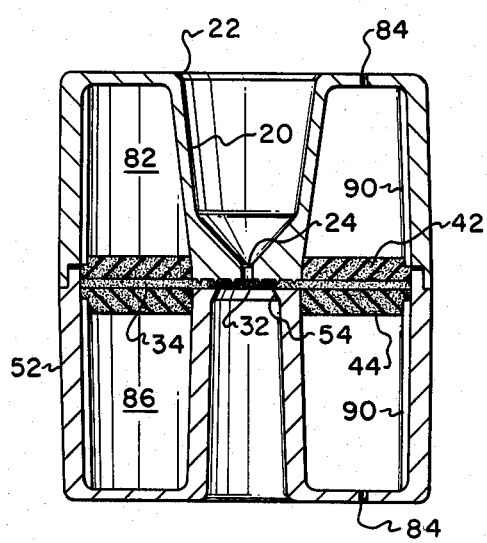
FIG. 4 is a cross-sectional view of an alternative embodiment of the test device having absorbent material above and below the filter means.

FIG. 4 shows a test device having absorbent material in contact with the upper and the lower peripheral faces of filter means 40.

Figure 5:
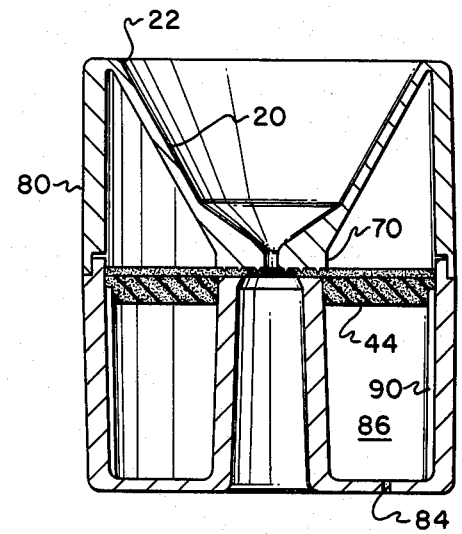
FIG. 5 is an alternative embodiment of the invention having an absorbent means below the filter means.

FIG. 5 shows an alternative embodiment in which absorbent means 40 is in contact with only the lower face of filter means 40.

Figure 6:
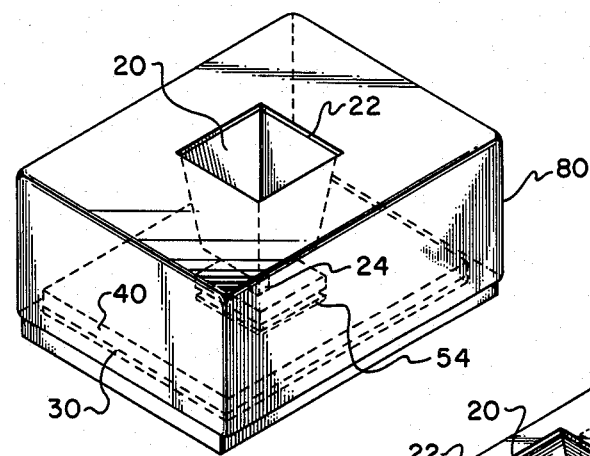
FIG. 6 is an alternative embodiment of the test device having a rectangular shape.

FIG. 6 shows a rectangular embodiment with rectangular shaped filter means 3 and with a rectangular absorbent skirt 40 surrounding discharge aperture 24.

Figure 7:
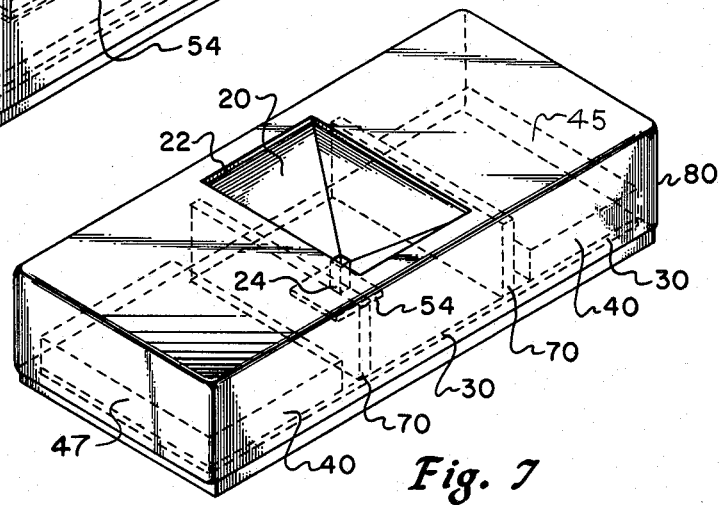
FIG. 7 is another alternative embodiment having absorbent material on either side of the liquid dispensing means.

FIG. 7 shows an embodiment in which a filter means 30 is rectangular and the absorbent means 40 comprises two separate absorbent means 45 and 47 in contact with portions of peripheral zone 34 on either side of the reaction zone 32.

FIG. 8 shows a rectangular embodiment similar to FIG. 6 but has liquid input means 20 positioned at one end of the structure and absorbent means in contact with one edge of peripheral zone 34.

FIG. 9 shows a rectangular embodiment in which liquid input means 20 is shaped as a trough containing a plurality of discharge apertures 24 in contact with filter means 40. A plurality of discrete reaction zones 32 are thereby created.

FIG. 10 shows an embodiment whereby a plurality of individual devices have been joined together to form a multipurpose, multiparametric system. A user can randomly select any desired units and snap or fasten them together.

One common inventive aspect of each of these alternative embodiments is that the filter means 30 is positioned below the input means 20 with at least one reaction zone 32 for receiving liquid from the input means 20 and having at least one peripheral zone 34 associated with the reaction zone 32. The absorbent means 40 is associated with only the peripheral zone 34 of the filter means 30 and the retainer means 50 holds the filter means in position below the liquid input means 20 such that the reaction zone receives liquid therefrom.

Further inventive aspects are that there is an enclosure means 52 corresponding in size and shape to the filter means 30 for holding the reaction zone 32 in alignment with the discharge aperture 24 and the enclosure means 52 has a port 54 in alignment with the reaction zone 32 for viewing the reaction zone 32 from below. Another aspect is that the receiving inlet 22 is larger than the discharge aperture so that liquid poured into the inlet 22 is funneled for localized discharge onto the reaction zone 32.

A unique aspect of the embodiment of FIGS. 7, 8, and 9 is that they lend themselves conveniently to multiply assay use. In such an application, each test device could contain a fastening means for removably or permanently attaching two or more devices together, side by side. This way a user could select from a stock of devices any one or several which are useful for the particular test to be done. Where the device has a component prespotted on the filter, for example, FIG. 7, a user could randomly select a device for each test to be performed in a series for a given patient, snap them together to form a unified set of devices, and run all the assays together. This use can be considered a multiparametric application because of the plurality of tests that can be performed with a number of devices.

Another novel aspect of this invention is shown by the embodiment in FIG. 9, wherein there are a plurality of reaction zones contained in a single device. As such, the device becomes more versatile where a plurality of reactions with the the same components are desired to measure consistency of results. Moreover, where filter means 30 is prespotted, a plurality of different components, for example, antibodies, could be contained in a single device. Therefore, a set of different multiparametric reactions could be carried out simultaneously using a common input means 22 to deliver sample and reactants to different discrete reaction zones.

It will be evident from the foregoing that the devices of the present invention can be inexpensively made and thus disposed after being used for one test; or, if desired, the device 10 can be opened by separating casing means 80 and enclosure means 52 and replacing used filter means 30 and absorbent means 40 with new counterparts and reassembling the device for a further test.

Also, the present device can be used with chromogenic assays such that the test results can be observed by the eye of the user of the device or the device can be used in conjunction with an automated reader such as a colorimeter for determination of the results.

The embodiments described and the alternative embodiments presented in the figures and in the detailed description of the drawings are intended as examples rather than as limitations. Thus, the description of the invention is not intended to limit the invention to the particular embodiments disclosed but it is intended to encompass all equivalents and subject matter within the spirit and scope of the invention as described above and as claimed in the claims which follow.

What is claimed is:

1. A device comprising: means for testing for the presence of an analyte in a liquid including:
 a. liquid input means having a receiving inlet and a discharge aperture;
 b. filter means positioned below said liquid input means and having at least one viewable reaction zone for receiving liquid from said input means to separate any analyte therefrom and at least one peripheral zone associated with said at least one reaction zone;

c. absorbent means associated with only said peripheral zone of said filter means for drawing said liquid from said reaction zone to said peripheral zone; and d. retainer means for holding said filter means in position below said liquid input means such that said at least one reaction zone receives liquid therefrom.

2. A test device as in claim 1 wherein said retainer means further comprises:

a. closure means corresponding in size and shape to said filter means for holding said reaction zone in alignment with said discharge aperture; and b. said closure means having a port in alignment with said reaction zone for viewing said reaction zone from below.

3. A test device as in claim 1 wherein said liquid input means receiving inlet is larger than said discharge aperture so that liquid poured into said inlet is funneled for localized discharge only on said reaction zone thereby causing said liquid to travel through said filter from said reaction zone to said peripheral zone.

4. A test device as in claim 1 wherein said filter means comprises a substantially flat porous material capable of drawing liquid through its structure by capillary action and having upper and lower faces positioned transversely to the direction of liquid flow from said liquid discharge aperture.

5. A test device as in claim 4 wherein said absorbent means comprises an absorbent skirt which abuts against the peripheral zone of the upper face of said flat porous filter material completely surrounding said reaction zone thereby allowing said liquid to travel outwardly through said filter pad from said reaction zone.

6. A test device as in claim 4 wherein said absorbent means comprises an absorbent skirt which abuts against the peripheral zone of said lower face of said porous filter material entirely surrounding said reaction zone.

7. A test device as in claim 4 wherein said absorbent means comprises a first absorbent skirt in contact with the peripheral zone of said upper face of said filter and a second absorbent skirt in contact with the peripheral zone of said lower face of said filter both entirely surrounding said reaction zone.

8. A test device as in claim 4 wherein said absorbent means comprises a first absorbent skirt portion in contact with a first portion of the peripheral zone of said upper face of said filter and a second absorbent skirt portion is contact with a second portion of the peripheral zone of said filter upper face separated from said first portion such that neither absorbent skirt portion entirely surrounds said reaction zone thereby drawing said liquid through said filter pad from said reaction zone to said peripheral zone.

9. A test device as in claim 1 further comprising a liquid impermeable shield contacting said filter means separating said reaction zone from said absorbent means so that liquid discharged on said reaction zone must pass through said reaction zone to reach said absorbent means.

10. A device comprising: means for testing for the presence of an analyte in a liquid including:

a. a liquid input means having at least one receiving inlet and at least one discharge aperture smaller than said at least one inlet so that liquid poured into said at least one inlet is funneled for localized discharge;

b. filter means positioned below said at least one discharge aperture having at least one reaction zone for receiving said liquid from said at least one discharge aperture and separating any analyte therefrom and at least one peripheral zone associated with said at least one reaction zone for receiving liquid therefrom;

c. absorbent means associated with only said peripheral zone of said filter means for absorbing liquid from said peripheral zone to draw said liquid from said reaction zone to said peripheral zone;

d. closure means for holding said filter means in alignment with said at least one discharge aperture; and e. said closure means having a viewing port in alignment with said at least one reaction zone for viewing said at least one reaction zone from below.

11. A test device as in claim 10 wherein the size of said discharge aperture is sufficiently small to limit the hydrostatic pressure in said liquid such that said liquid flowing through said filter means from said reaction zone to said peripheral zone does not escape through said viewing port so that no covering is required over said viewing port during use of the test device.

12. A test device as in claim 10 further comprising casing means, including said input means and said closure means, for encasing said filter means, and said absorbent means so that said test device can be manipulated without contacting any liquid contained therein.

13. The test device of claim 10 wherein the portion of said liquid input means which defines said liquid discharge aperture is in intimate contact with said reaction zone.

14. A test device as in claim 10 further comprising a liquid impermeable shield contacting said filter means separating said reaction zone from said absorbent means so that liquid discharged on said reaction zone must pass through said reaction zone to be drawn into said absorbent means.

15. A test device as in claim 10 wherein said input means has a plurality of discharge apertures each contacting said filter surface creating a corresponding plurality of said reaction zones.

16. A test device as in claim 10 wherein said input means is positioned at one end of said device so that said absorbent means is positioned so as to contact a side of said peripheral zone.

17. A system of test devices as in claim 10 wherein a plurality of said test devices are permanently joined together so as to form a combined set of devices suitable for multiparametric use.

18. A system of test devices as in claim 10 wherein a plurality of said test devices are removably joined together so as to form a combined set of devices suitable for multiparametric use.

19. A device as in claim 10 wherein said filter means comprises a substantially planer porous material capable of drawing liquid through its pores by capillary action.

20. The test device of claim 19 wherein said filter means is capable of effecting a filter separation of an insolubilized component from a solubilized component when a liquid is applied to said filter means and wicked through its pores by capillary action.

21. The test device of claim 20 wherein said filter means has in said at least one reaction zone an area capable of supporting an immunological reaction.

22. The test device of claim 21 wherein said filter means is composed of glass fiber filter paper.

23. A test device as in claim 20 wherein said filter means comprises:
  a. a micro-porous membrane having substantially uniform pores between 25 nanometers and 25 micrometers, said pores defining integral surfaces in said membrane; and
  b. an analyte specific reactant immobilized on said integral surfaces of said reaction zone of said micro-porous membrane.

24. A device comprising: means for testing for the presence of an analyte in a liquid including:
  a. a liquid input means having an upper receiving inlet and a lower discharge aperture smaller than said receiving inlet;
  b. filter means positioned below said liquid input means and having at least one reaction zone and having at least one peripheral zone integrally formed of a substantially planar porous material having upper and lower faces which porous material is capable of drawing liquid through its pores by capillary action so that liquid discharged into said reaction zone is drawn into said peripheral zone;
  c. an absorbent skirt in contact with only said peripheral zone of said planar porous material, said porous material entirely surrounding said reaction zone so that liquid drawn from said reaction zone into said peripheral zone is absorbed by said absorbent skirt;
  d. closure means connected to said liquid input means and contacting said lower face of said reaction zone for holding said upper face of said reaction zone in alignment for fluid flow communication with said discharge aperture, said closure means having a viewing port therein for viewing at least a portion of said lower face of said reaction zone;
  e. a substantially liquid impermeable shield means positioned adjacent said liquid discharge aperture for abutting against said upper face of said reaction zone means and for separating said absorbent skirt from said discharge aperture so that liquid from said aperture passes outwardly through at least a portion of said reaction zone; and
  f. a casing means attached to said input means receiving inlet and connected to said closure means for encasing said test device so that said test device can be manipulated for observing said reaction zone through either said viewing port or said input means without contacting said absorbent skirt or said filter means.

25. A test device as in claim 24 wherein:
  a. said absorbent skirt comprises a compressed sponge material which is capable of expanding to absorb liquid upon contact therewith; and
  b. said casing means forms a hollow cavity positioned such that said compressed sponge material may expand into said cavity upon contact with liquid from said peripheral zone of said filter means.

26. The test device of claim 25 wherein said hollow cavity contains a vent therein to permit equalization of air pressure upon expansion of absorbent skirt into said cavity.

27. A test device as in claim 24 wherein said absorbent skirt is a hollow cylinder of absorbent material of substantially uniform thickness with the base thereof in contact with the peripheral portion only of said upper face of said filter means entirely surrounding said upper face of said reaction zone substantially equidistant from the reaction zone at which liquid is received from said liquid discharge aperture so that said liquid is drawn substantially uniformly in each transverse radial direction through said reaction zone.

28. A test device as in claim 27 wherein said filter means has a circular disc shape with an outside diameter corresponding to the outer diameter of said hollow cylinder absorbent skirt to promote uniformity of liquid flow outwardly through said filter.

29. A test device as in claim 28 wherein:
  a. said hollow absorbent cylinder is composed of a compressed sponge material which is capable of expanding to absorb liquid upon contact therewith; and
  b. said casing means forms a hollow cavity positioned above said absorbent cylinder such that said compressed sponge material may expand into said cavity upon contact with liquid from said peripheral zone of said filter means.

30. A test device as in claim 29 further comprising at least one projection from the interior of said hollow cavity having sufficient height to restrict movement of said compressed sponge and to hold said sponge in contact with said filter in its compressed state and to permit expansion of said sponge into said cavity upon absorbing liquid as by plastic deformation of said sponge around said projections while maintaining said sponge in contact with said filter.

31. A test device as in claim 24 wherein:
  a. said absorbent skirt comprises a hollow cylinder of substantially uniform thickness sponge material capable of expanding axially to absorb liquid, which absorbent cylinder is in contact with the lower face of said peripheral zone; and
  said filter means has a circular disc shape with an outside diameter corresponding to the outer diameter of said hollow cylinder absorbent skirt to promote uniformity of transverse liquid flow outwardly through said filter means.

32. A test device as in claim 31 wherein said closure means having a port centrally located therein forms a hollow cavity attached to said liquid input means surrounding said absorbent skirt so that said absorbent skirt may expand into said cavity upon absorbing liquid drawn outwardly from said porous reaction zone.

33. A test device as in claim 24 wherein said absorbent skirt comprises absorbent material in contact with the periphery of both said upper and said lower reaction zone faces.

34. A test device as in claim 24 wherein said input means forming said discharge aperture has a bottom end surrounding said discharge aperture in intimate contact with said filter means upper face, thereby forming said liquid impermeable shield means.

35. A test device as in claim 34 wherein said bottom end of said input means forming said shield is permanently affixed to said filter means' upper surface.

36. A test drive as in claim 34 wherein said bottom end of said input means forming said shield means further comprises a substantially flat surface having at least one circular serration thereon which circular serration is in intimate contact with said filter means completely surrounding said discharge aperture.

37. A test device as in claim 36 wherein said at least one circular serration comprises multiple concentric circular serrations in intimate contact with said filter means.

38. A test device as in claim 36 wherein said bottom surface provides a reaction reading surface.

39. A test device as in claim 38 wherein said reaction surface comprises a light-reflecting surface.

40. A test device as in claim 38 wherein said reading surface comprises a light-absorbing surface.

41. A test device as in claim 38 wherein said reading surface comprises a light-transmitting surface.

* * * * *

UNITED STATES PATENT AND TRADEMARK OFFICE
CERTIFICATE OF CORRECTION

PATENT NO. : 4,623,461
DATED : Nov. 18, 1986
INVENTOR(S) : Hossom and Jacob

It is certified that error appears in the above-identified patent and that said Letters Patent are hereby corrected as shown below:

Column 3, line 7, "member" should read --means--.

Column 7, line 28, "said" should read --same--.

Claim 8 (Column 11, line 53) "is" should read --in--.

Claim 31 (Column 14, line 38) insert --b.-- at the beginning of the paragraph.

Signed and Sealed this

Tenth Day of February, 1987

*Attest:*

DONALD J. QUIGG

*Attesting Officer*      *Commissioner of Patents and Trademarks*